(12) United States Patent
Hossainy et al.

(10) Patent No.: US 9,220,759 B2
(45) Date of Patent: Dec. 29, 2015

(54) TREATMENT OF DIABETIC PATIENTS WITH A DRUG ELUTING STENT AND ADJUNCTIVE THERAPY

(75) Inventors: Syed F. A. Hossainy, Hayward, CA (US); Paul M. Consigny, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 681 days.

(21) Appl. No.: 13/403,709

(22) Filed: Feb. 23, 2012

(65) Prior Publication Data

US 2013/0224255 A1  Aug. 29, 2013

(51) Int. Cl.

| A61K 9/00 | (2006.01) |
|---|---|
| A61K 38/28 | (2006.01) |
| A61F 2/82 | (2013.01) |
| A61K 31/436 | (2006.01) |
| A61K 31/426 | (2006.01) |
| A61K 31/4365 | (2006.01) |
| A61K 31/45 | (2006.01) |
| A61K 31/4709 | (2006.01) |
| A61K 31/506 | (2006.01) |
| A61K 31/519 | (2006.01) |
| A61K 31/553 | (2006.01) |
| A61K 31/565 | (2006.01) |
| A61K 31/573 | (2006.01) |
| A61K 31/65 | (2006.01) |
| A61K 45/06 | (2006.01) |
| A61K 35/58 | (2015.01) |
| A61K 38/58 | (2006.01) |

(52) U.S. Cl.
CPC . *A61K 38/28* (2013.01); *A61F 2/82* (2013.01); *A61K 31/426* (2013.01); *A61K 31/436* (2013.01); *A61K 31/4365* (2013.01); *A61K 31/45* (2013.01); *A61K 31/4709* (2013.01); *A61K 31/506* (2013.01); *A61K 31/519* (2013.01); *A61K 31/553* (2013.01); *A61K 31/565* (2013.01); *A61K 31/573* (2013.01); *A61K 31/65* (2013.01); *A61K 35/58* (2013.01); *A61K 45/06* (2013.01); *A61F 2250/0067* (2013.01); *A61K 38/58* (2013.01)

(58) Field of Classification Search
CPC ..... A61K 31/436; A61K 35/58; A61K 45/06; A61K 38/58; A61K 31/426; A61K 31/4365; A61K 31/45; A61K 31/4709; A61K 31/506; A61K 31/519; A61K 31/553; A61K 31/565; A61K 31/573; A61K 31/65; A61F 2/82; A61F 2250/0067

See application file for complete search history.

(56) References Cited

U.S. PATENT DOCUMENTS

| 5,049,132 | A | 9/1991 | Shaffer et al. |
|---|---|---|---|
| 5,646,160 | A | 7/1997 | Morris et al. |
| 5,843,172 | A | 12/1998 | Yan |
| 6,015,815 | A | 1/2000 | Mollison |
| 6,096,070 | A | 8/2000 | Ragheb et al. |
| 6,239,124 | B1 | 5/2001 | Zenke et al. |
| 6,329,386 | B1 | 12/2001 | Mollison |
| 6,663,880 | B1 | 12/2003 | Roorda et al. |
| 6,890,546 | B2 | 5/2005 | Mollison et al. |
| 6,939,376 | B2 | 9/2005 | Shulze et al. |
| 7,357,942 | B2 | 4/2008 | Burke et al. |
| 7,378,105 | B2 | 5/2008 | Burke et al. |
| 7,399,480 | B2 | 7/2008 | Mollison et al. |
| 7,445,792 | B2 | 11/2008 | Toner et al. |
| 7,758,881 | B2 * | 7/2010 | Dugan .......................... 424/423 |
| 7,769,420 | B2 * | 8/2010 | Silver et al. ................... 600/345 |
| 7,959,659 | B2 | 6/2011 | Ding |
| 8,048,441 | B2 | 11/2011 | Craig et al. |
| 8,092,822 | B2 | 1/2012 | Pacetti et al. |
| 8,114,968 | B2 * | 2/2012 | Devy et al. ............... 530/388.26 |
| 2001/0051166 | A1 | 12/2001 | Luo et al. |
| 2002/0037919 | A1 | 3/2002 | Hunter et al. |
| 2003/0191179 | A1 | 10/2003 | Joshi-Hangal et al. |
| 2005/0142202 | A1 | 6/2005 | Roorda et al. |
| 2005/0282734 | A1 | 12/2005 | Kadima et al. |
| 2005/0287184 | A1 | 12/2005 | Hossainy et al. |
| 2006/0002968 | A1 | 1/2006 | Stewart et al. |
| 2006/0020243 | A1 | 1/2006 | Speck et al. |
| 2006/0045901 | A1 | 3/2006 | Weber et al. |
| 2006/0105019 | A1 | 5/2006 | Stewart et al. |
| 2006/0136048 | A1 | 6/2006 | Pacetti et al. |
| 2006/0147489 | A1 | 7/2006 | Shanley et al. |
| 2006/0206149 | A1 * | 9/2006 | Yun ................................... 607/3 |

(Continued)

FOREIGN PATENT DOCUMENTS

| WO | WO 02/32347 | 4/2002 |
|---|---|---|
| WO | WO 03/037355 | 5/2003 |

(Continued)

OTHER PUBLICATIONS

Gosh et al. "Skin permeation of rosiglitazone from transdermal matrix patches," Pharmaceutical Technology, vol. 34, Issue 5, May 2, 2010.*

(Continued)

*Primary Examiner* — Suzanne Ziska
(74) *Attorney, Agent, or Firm* — Squire Patton Boggs (US) LLP (57) ABSTRACT

Embodiments of the present invention include methods for the treatment, prevention, or amelioration of vascular disease in diabetic patients. The methods include both implantation of a stent including a first drug. Some embodiments include additional therapy, such as the co-administration of another drug. Some embodiments involve different stent selection for a diabetic patient compared to a non-diabetic patient.

29 Claims, 1 Drawing Sheet

(56) References Cited

U.S. PATENT DOCUMENTS

| | | | |
|---|---|---|---|
| 2007/0026035 A1* | 2/2007 | Burke et al. | 424/423 |
| 2007/0083258 A1* | 4/2007 | Falotico et al. | 623/1.42 |
| 2007/0224240 A1 | 9/2007 | Toner et al. | |
| 2007/0244549 A1 | 10/2007 | Pathak et al. | |
| 2008/0004694 A1 | 1/2008 | Mack et al. | |
| 2008/0145402 A1 | 6/2008 | Mollison et al. | |
| 2008/0167711 A1 | 7/2008 | Roorda | |
| 2008/0181927 A1 | 7/2008 | Zhao et al. | |
| 2009/0104247 A1 | 4/2009 | Pacetti et al. | |
| 2009/0203602 A1 | 8/2009 | Gelber et al. | |
| 2009/0286761 A1 | 11/2009 | Cheng et al. | |
| 2010/0023108 A1 | 1/2010 | Toner et al. | |
| 2010/0233236 A1* | 9/2010 | Zhao | 424/423 |
| 2010/0331819 A1 | 12/2010 | Hossainy et al. | |
| 2011/0160575 A1 | 6/2011 | Beyar et al. | |
| 2011/0184384 A1 | 7/2011 | Davalian et al. | |
| 2011/0229548 A1 | 9/2011 | Lim et al. | |
| 2011/0275980 A1 | 11/2011 | Weber et al. | |
| 2012/0035150 A1 | 2/2012 | Gaweco et al. | |
| 2012/0122838 A1 | 5/2012 | Ren et al. | |
| 2012/0263759 A1 | 10/2012 | Hossainy et al. | |
| 2013/0259921 A1 | 10/2013 | Hossainy et al. | |
| 2013/0261722 A1 | 10/2013 | Hossainy et al. | |
| 2013/0261723 A1 | 10/2013 | Stankus et al. | |
| 2013/0303496 A1 | 11/2013 | Cox et al. | |

FOREIGN PATENT DOCUMENTS

| | | |
|---|---|---|
| WO | WO 2005/097186 | 10/2005 |
| WO | WO 2008/076847 | 6/2008 |

OTHER PUBLICATIONS

U.S. Appl. No. 13/436,303, filed Mar. 30, 2012, Hossainy.
U.S. Appl. No. 13/435,645, filed Mar. 30, 2012, Hossainy.
U.S. Appl. No. 13/436,662, filed Mar. 30, 2012, Stankus et al.
U.S. Appl. No. 13/466,504, filed May 8, 2012, Cox et al.
Ajjan et al., "Cardiovascular disease prevention in patients with type 2 diabetes: the role of oral anti-diabetic agents", Diabetes Vasc. Dis. Res. 3, pp. 147-158 (2006).
Berry et al., "Coronary Heart Disease in Patients with Diabetes", J. of the Am. College of Cardiology vol. 49, No. 6, pp. 643-644 (2007).
Cardiovascular disease, downloaded: www.answers.com/topic/cardiovascular-disease, Aug. 12, 2012, 19 pages.
Cardiovascular disease, downloaded: www.bhf.org.uk/heart-health/conditions/cardiovascular-disease.aspx, Aug. 12, 2012, 2 pgs.
Cardiovascular disease, downloaded: www.wikipedia.org/wiki/Cardiovascular_disease, Aug. 12, 2012, 11 pgs.
Coronary heart disease, MedlinePlus, downloaded: www.nlm.nih.gov/medlineplus/ency/article, Aug. 12, 2012, 5 pgs.
Definition of Cardiovascular disease. downloaded: www.medterms.com/script/main/art.asp?articlekey, Aug. 12, 2012, 3 pgs.
Hage et al., "Glycaemic control and restenosis after percutaneous coronary interventions in patients with diabetes mellitus: a report from the Insulin Diabetes Angioplasty study", Diabetes & Vascular Disease Res. 6(2) 71-79 (2009).
Hage et al., "The predictive value of inflammatory activity and markers of the adipo-insular axis on restenosis in patients with type 2 diabetes", Diabetes & Vascular Disease Res. 8(2) 143-149 (2011).
Hong et al., "Multiple predictors of coronary restenosis after drug-eluting stent implantation in patiets with diabetes", Heart 92, pp. 1119-1124 (2006).
Letchford, "A review of the formation and classification of amphiphilic block copolymer nanoparticulate structures: micelles, nanospheres, nanocapsules and polymersomes", EU J. of Pharm. and biopharmaceutics vol. 65, issue 3, pp. 259-269 (2007).
Libby "Inflammation and cardiovascular disease mechanisms", Am. J. Clin. Nutr. 83 suppl. pp. 456S-460S (2006).
Libby et al., "Inflamation in Diabetes Melltus: Role of Peroxisome Proliferator-Activated Receptor-$\alpha$ and Peroxisome Proliferator-Activated Receptor-$\gamma$ Agonists", The Am. J. of Card. vol. 99 (4A) pp. 27B-28B (2007).
Nissen "Pioglitazone to Reduce Restenosis After Bare-Metal Stent Placement?", JACC vol. 2, No. 6, pp. 532-533 (2009).
Opsteen et al., "Block copolymer vesicles", Pure Appl. Chem. vol. 76, No. 7-8, pp. 1309-1319 (2004).
Philpott et al., "Long-term outcomes of patients receiving drug-eluting stents", CMAJ 180 (2) pp. 167-168 (2009).
Shan et al., "Leptin-enhanced neointimal hyperplasia is reduced by mTOR and P13K inhibitors", PNAS vol. 105, No. 48 pp. 19006-19011 (2008).
Sobel "Acceleration of Restenosis by Diabetes, Pathogenetic Implications", J. of the Am. Heart Assoc., Circulation 103, pp. 1185-1187 (2001).
Ta-Jen Liu et al., "NVP-BEZ235, a novel dual prhosphatidylinositol 3-kinase/mammalian target of rapamycin inhibitor, elicits multifaceted antitumor activities in human gliomas", Mol. Cncer Ther. 8(8), pp. 2204-2210 (2009).
Takagi et al., "A prospective, Multicenter, Randomized Trial to Assess Efficacy of Pioglitazone on In-Stent Neointimal Suppression in Type 2 Diabetes", JACC Cardiovascular Interventions vol. 2, No. 6, pp. 524-531 (2009).
The Heart and Vascular Disease. downloaded: www.medicinenet.com/vascular_disease/article.htm, Aug. 12, 2012, 4 pgs.
Vascular disease, downloaded: www.wikipedia.org/wiki/Vascular_disease, Aug. 12, 2012, 3 pgs.
What is a vascular disease? downloaded: www.clevelandclinic.org/heart/disorders/vascular/whatis.aspx, Aug. 12, 2012, 4 pgs.
What is Cardiovascular disease (Heart Disease)? Downloaded: www.heart.org/HEARTORG/Caregiver/Resources/WhatisCardiovascularDisease/W, Aug. 12, 2012, 2 pgs.
What is Cardiovascular disease? downloaded: www.news-medical.net/health/What-is-Cardiovascular-disease.aspx, Aug. 12, 2012, 3 pgs.
"Diagnosis and Classification of Diabetes Mellitus", Diabetes Care vol. 27, No. suppl. 1, pp. S5-S10 (2004).
"Diagnosis of Diabetes and Prediabetes", National Diabetes Information Clearinghouse (NDIC), downloaded from: www.diabetes.niddk.nih.gov/dm/pubs/diagnosis/, Feb. 1, 2013 11 pgs.
"Heart Disease", American Diabetes Association, downloaded from: www.diabetes.org/living-with-diabetes/complications/heart-disease, Jan. 31, 2013, 2 pgs.
Jackson Behan, "New ADA Guidelines for Diagnosis, Screening of Diabetes", Advance Laboratory vol. 20, issue 1, downloaded from: www.laboratory-manager.advanceweb.com/Archives/Article-Archives/New-ADA-Gudelin. Feb. 1, 2013, 4 pgs.
RIDAFOROLIMUS, Statement on a Nonproprietary Name Adopted by the USAN Council, 1 page.
Medtronic (What to Expect—Getting a Stent, Sep. 22, 2010), 3 pages.
HeartSite.com (Balloon Angioplasty, Aug. 8, 2002), 3 pages.

* cited by examiner

TREATMENT OF DIABETIC PATIENTS WITH A DRUG ELUTING STENT AND ADJUNCTIVE THERAPY

BACKGROUND OF THE INVENTION

1. Field of the Invention

This invention relates to methods of treating vascular disease in diabetic patients.

2. Description of the State of the Art

Until the mid-1980s, the accepted treatment for coronary atherosclerosis, i.e., narrowing of the coronary artery(ies) was coronary by-pass surgery. While being quite effective and having evolved to a relatively high degree of safety for such an invasive procedure, by-pass surgery still involves potentially serious complications and in the best of cases an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it other problems such as vasospasm and elastic recoil of the stretched arterial wall which could undo much of what was accomplished and, in addition, created a new problem, restenosis, the re-clogging of the treated artery due to neointimal hyperplasia, that is, abnormal regrowth of the inner lining of the vessel after treatment with PTCA.

The next improvement, advanced in the mid-1980s, was the use of a stent to maintain the luminal diameter after PTCA. This for all intents and purposes put an end to vasospasm and elastic recoil but did not entirely resolve the issue of restenosis. That is, prior to the introduction of stents, restenosis occurred in from about 30 to 50% of patients undergoing PTCA. Stenting reduced this to about 15 to 20%, a substantial improvement but still more than desirable. For diabetic patients, however, the incidence of restenosis after stenting and major cardiac events were significantly higher than for non-diabetics patients.

In 2003, drug-eluting stents or DESs were introduced. The drugs initially employed with the DES were cytostatic compounds that curtailed the proliferation of cells that resulted in restenosis. The occurrence of restenosis was reduced to about 5 to 7%, a relatively acceptable figure. However, the rate of restenosis with DES is still higher for diabetic patients than non-diabetic patients. In addition, the use of DESs engendered yet another complication, late stent thrombosis, the forming of blood clots long after the stent was in place. It has been hypothesized that the formation of blood clots was most likely due to delayed healing, a side-effect of the use of cytostatic drugs.

Thus, there is a need for improved methods for treating vascular disease in diabetic patients.

SUMMARY OF THE INVENTION

The present invention is directed to methods of treating vascular disease in diabetic patients, the methods involving the implantation of a stent.

Various non-limiting embodiments of the present invention are described in the following numbered paragraphs, paragraphs (1) to (41):

(1) A method of treating, preventing, or ameliorating a vascular disease in a diabetic patient, the method including implanting a stent in a vascular region of a diabetic patient.

(2) The method according to paragraph (1), wherein the stent is selected to have a higher surface area at the edges than in the middle of the stent.

(3) The method according to any one of paragraphs (1) and (2), wherein the stent is selected to have a length that is about 2 mm to about 8 mm, about 3 mm to about 7 mm, about 4 mm to about 6 mm, or about 5 mm, or 5 mm greater in length in both directions than the length of a stent that would be selected for a non-diabetic patient.

(4) The method according to any one of paragraphs (1)-(3), further including administering a food or food supplement of complex carbohydrates to the diabetic patient for a time period ranging from 2 weeks to 12 months and the time period encompassing the time of stent implantation.

(5) The method according to any one of paragraphs (1)-(4), wherein the stent includes a first drug, and the first drug is an anti-inflammatory, an antiproliferative, an antineoplastic, an antimitotic, an antiplatelet, an anticoagulant, an antifibrin, an antithrombin, antibiotic, an anti-allergic, an antioxidant substance, or any combination thereof.

(6) The method according to any one of paragraphs (1)-(5), further including administering a second drug to the diabetic patient, and the second drug reduces inflammation, reduces the amount, activity, or both the amount and activity of tumor necrosis factor alpha, improves the responsiveness of the artery to insulin, reduces platelet activation, reduces fluctuation in hemoglobin A1C, reduces tissue factor activity, reduces thrombin activity, or any combination thereof.

(7) The method according to any one of paragraphs (6), wherein the second drug is administered over a definite time period.

(8) The method according to paragraph (7), wherein the second drug is administered orally, transdermally, or both orally and transdermally.

(9) The method according to any one of paragraphs (7) and (8), wherein the definite time period begins at least at the time of the implantation of the stent.

(10) The method according to any one of paragraphs (7)-(9), wherein the definite time period begins at least 7 days or at 7 days prior to the implantation of the stent.

(11) The method according to any one of paragraphs (7)-(9), wherein the definite time period begins within 1 to 30 days prior to the implantation of the stent.

(12) The method according to any one of paragraphs (7)-(11), wherein the definite time period ends at least 1 month after the implantation of the stent.

(13) The method according to any one of paragraphs (7)-(11), wherein the definite time period ends at least 6 months after the implantation of the stent.

(14) The method according to any one of paragraphs (7)-(11), wherein the definite time period ends at 6 months after the implantation of the stent or at about 6 months after the implantation of the stent.

(15) The method according to any one of paragraphs (7)-(11), wherein the definite time period ends within 1 week to 12 months after the implantation of the stent.

(16) The method according to paragraph (7), wherein the second drug is administered by subcutaneous or intravenous injection.

(17) The method according to any one of paragraphs (7) and (16), wherein the definite time period begins at least 2 hours prior to the implantation of the stent.

(18) The method according to any one of paragraphs (7) and (16), wherein the definite time period begins within 1 to 24 hours prior to implantation of the stent.

(19) The method according to any one of paragraphs (7), (16) and (17), wherein the definite time period ends at 2 hours after implantation of the stent.

(20) The method according to any one of paragraphs (7), (16) and (17), wherein the definite time period ends within 1 to 24 hours after implantation of the stent.

(21) The method according to paragraph (7), wherein the second drug is administered intra-arterially via an introducer, a catheter, or both an introducer and a catheter.

(22) The method according to any one of paragraphs (7)-(15), wherein the second drug is administered orally and the second drug is an anti-microbial.

(23) The method according to any one of paragraphs (7)-(15), wherein the second drug is administered orally and the second drug is doxycycline.

(24) The method according to any one of paragraphs (7)-(15), wherein the second drug is administered orally, transdermally, or both orally and transdermally and the second drug is a glitazone.

(25) The method according to any one of paragraphs (7)-(15), wherein the second drug is administered orally, and the second drug is cilostazol, prasugrel, tigacrelor, or a combination thereof.

(26) The method according to any one of paragraphs (7)-(15), wherein the second drug is administered orally, and the second drug is an anti-IL-6.

(27) The method according to any one of paragraphs (7)-(15), wherein the second drug is administered transdermally, and is an anti-TNF biologic.

(28) The method according to any one of paragraphs (7) and (16)-(20), wherein the second drug is administered intravenously and is an anti-microbial.

(29) The method according to any one of paragraphs (7) and (16)-(20), wherein the second drug is doxycycline.

(30) The method according to paragraph (7), wherein the second drug is administered subcutaneously.

(31) The method according to any one of paragraphs (7) and (20), wherein the definite time period begins at 2 hours or at about 2 hours prior to the stent deployment.

(32) The method according to any one of paragraphs (30) and (31), wherein the definite time period ends at 2 hours or at about 2 hours after stent deployment.

(33) The method according to any one of paragraphs (3)-(7), wherein the second drug is adalimumab, and it is administered subcutaneously at about 2 hours prior to stent deployment, during stent deployment, and at about 2 hours after stent deployment.

(34) The method according any one of paragraphs (7) and (30), wherein the second drug is insulin, and the definite time period begins within 12 hours to 7 days prior to stent implantation, and ends within 9 to 18 months after stent implantation.

(35) The method according to any one of paragraphs (3)-(33), wherein the second drug is administered at a dose such that the plasma concentration is lower than the lower end of the therapeutic range for normal use.

(36) The method according to any one of paragraphs (3)-(33), wherein the second drug is administered at a dose such that the plasma concentration is within the range of 20% and 80% of the lower end of the therapeutic range for normal use.

(37) The method according to any one of paragraphs (3)-(33), wherein the second drug is administered in one or more cycles, each cycle including administration at a first dose such that the plasma concentration is within the therapeutic range for normal use, and then a subsequent administration at a second lower dose such that the plasma concentration is below the lower end of the therapeutic range for normal use.

(38) The method according to paragraph (37), wherein for at least one cycle, the subsequent administration at a second lower dose is such that the plasma concentration is within the range of 10% to 90% of the lower end of the therapeutic range for normal use.

(39) The method according to any one of paragraphs (37) and (38), wherein there are at least two cycles.

(40) The method according to any one of paragraphs (5)-(39), wherein the first drug is selected from the group consisting of rapamycin (sirolimus), Biolimus A9 (Biosensors International, Singapore), deforolimus, AP23572 (Ariad Pharmaceuticals), tacrolimus, temsirolimus, pimecrolimus, novolimus, zotarolimus (ABT-578), 40-O-(2-hydroxyl) ethyl-rapamycin (everolimus), 40-O-(3-hydroxypropyl)rapamycin 40-O-[2-(2-hydroxy)ethoxy]ethyl-rapamycin, 40-O-tetrazolylrapamycin, 40-epi-(N1-tetrazolyl)-rapamycin, dexamethasone, myolimus, actinomycins, taxol, paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

(41) The method of any one of paragraphs (5)-(40), wherein the stent including the first drug includes a coating, with at least a portion of the first drug included in the coating.

DETAILED DESCRIPTION OF THE INVENTION

Use of the term "herein" encompasses the specification, the abstract, and the claims of the present application.

Use of the singular herein includes the plural and vice versa unless expressly stated to be otherwise, or obvious from the context that such is not intended. That is, "a" and "the" refer to one or more of whatever the word modifies. For example, "a drug" includes one drug, two drugs, etc. Likewise, "the polymer" may refer to one, two or more polymers, and "the stent" may mean one stent or a plurality of stents. By the same token, words such as, without limitation, "polymers" and "stents" would refer to one polymer or stent as well as to a plurality of polymers or stents unless, again, it is expressly stated or obvious from the context that such is not intended.

As used herein, unless specifically defined otherwise, any words of approximation such as without limitation, "about," "essentially," "substantially," and the like mean that the element so modified need not be exactly what is described but can vary from the description. The extent to which the description may vary will depend on how great a change can be instituted and have one of ordinary skill in the art recognize the modified version as still having the properties, characteristics and capabilities of the unmodified word or phrase. In general, but with the preceding discussion in mind, a numerical value herein that is modified by a word of approximation may vary from the stated value by ±15%, unless expressly stated otherwise.

As used herein, any ranges presented are inclusive of the end-points. For example, "a temperature between 10° C. and 30° C." or "a temperature from 10° C. to 30° C." includes 10° C. and 30° C., as well as any specific temperature in between.

As used herein, the use of "preferred," "preferably," or "more preferred," and the like to modify an aspect of the invention refers to preferences as they existed at the time of filing of the patent application.

As used herein, a "polymer" is a molecule made up of the repetition of a simpler unit, herein referred to as a constitutional unit. The constitutional units themselves can be the product of the reactions of other compounds. A polymer may comprise one or more types of constitutional units. As a non-limiting example, ethylene ($CH_2=CH_2$) is a monomer that can be polymerized to form the polymer, polyethylene, $CH_3CH_2(CH_2CH_2)_nCH_2CH_3$ (where n is an integer), wherein the constitutional unit is —$CH_2CH_2$—, ethylene having lost the double bond as the result of the polymerization reaction. As used herein, the term polymer refers to a molecule comprising 20 or more constitutional units, where those molecules of fewer than 20 constitutional units are oligomers, and wherein the smallest repeating unit is used to determine the number of constitutional units. Polymers may have a random disposition of constitutional units along the chain, the constitutional units may be present as discrete blocks or segments, or constitutional units may be so disposed as to form gradients of concentration along the polymer chain. Polymers may be cross-linked to form a network.

As used herein, "copolymer" refers to a polymer which includes more than one type of constitutional unit. "Terpolymers" are a subset of copolymers in which there are three constitutional units.

As used herein, a material that is described as a layer, a film, or a coating "disposed over" a substrate refers to deposition of the material directly or indirectly over at least a portion of the surface of that substrate. "Directly deposited" means that the material is applied directly to the surface of the substrate. "Indirectly deposited" means that the material is applied to an intervening layer that has been deposited directly or indirectly over the substrate. The terms "layer," "film," and "coating" are used interchangeably herein. A coating may have multiple layers, and each layer may be applied by multiple applications of coating material. Layers typically differ from each other in the type of materials, the ratio of materials, or both the type of and the ratio of materials applied to form the layer. Materials may migrate from one layer to another layer during the coating application process, after the coating has been formed, or both during the coating application process and after the coating has been formed.

As used herein, a "drug" refers to a substance that, when administered in a therapeutically effective amount to a patient suffering from a disease or condition, has a therapeutic beneficial effect on the health and well-being of the patient. A therapeutic beneficial effect on the health and well-being of a patient includes, but it not limited to: (1) curing the disease or condition; (2) slowing the progress of the disease or condition; (3) causing the disease or condition to retrogress; or, (4) alleviating, ameliorating or both alleviating and ameliorating one or more symptoms of the disease or condition.

As used herein, the terms "biodegradable", "bioerodable", "bioabsorbable," "degraded," "eroded," "absorbed," and "dissolved," are used interchangeably, and refer to a substance that is capable of being completely or substantially completely, degraded, dissolved, eroded, or any combination thereof, over time when exposed to physiological conditions (pH, temperature, enzymes and the like), and can be gradually eliminated by the body, or that can be degraded into fragments that can pass through the kidneys. Conversely, "biostable" refers to a substance that is not biodegradable, etc.

As used herein, a "drug" also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "drug" also refers to pharmaceutically acceptable, pharmacologically active derivatives of those drugs specifically mentioned herein, including, but not limited to, salts, esters, amides, hydrates, solvates, and the like.

As used herein, the phrase "drug is X" refers also to pharmaceutically acceptable, pharmacologically active derivatives of the drug X, such as, but not limited to, salts, esters, amides, hydrates, solvates, and the like. As a non-limiting an example, "the drug is metformin" would also encompass metformin hydrochloride.

As used herein, "drug" also includes biologics that are presently regulated as drugs by the Center for Drug Evaluation and Research of the United States Food and Drug Administration (FDA), but excludes biologics that are presently regulated by the Center for Biologics Evaluation and Research of the FDA. Non-limiting examples of biologics included in the definition of a "drug" as used herein are "monoclonal antibodies designed as targeted therapies in cancer and other diseases, cytokines (types of proteins involved in immune response), growth factors (proteins that affect the growth of a cell), enzymes (types of proteins that speed up biochemical reactions)" for example, thrombolytics, that are "used to dissolve blood clots," and immunomodulators (agents that affect immune response)." Non-limiting examples of biologics that are excluded from the definition of a "drug" as used herein are allergy shots and tests, blood and blood components, human tissues and cellular products used in transplantation, gene therapy products, and vaccines.

Drugs may be administered by a number of routes which may be divided into two general categories, enteral administration and parenteral administration. Enteral administration is administration within or by way of the gastrointestinal tract, also known as the alimentary canal. Enteral administration includes, without limitation, oral, buccal, sublingual, and rectal administration.

Oral administration is administration into the mouth or administration into the mouth with swallowing. Oral administration includes the administration of solid oral dosage forms, liquid dosage forms, gels, pastes, sprays, or any combination thereof. Solid oral dosage forms include, without limitation, capsules, both hard shell and soft shell, tablets, pills, powders, and granules. Liquid dosage forms for oral administration include emulsions, solutions, suspensions, syrups and elixirs. Granules or powders may be reconstituted as an oral suspension or solution for administration.

Buccal administration is administration by absorption into the gum, into the check, or both. Sublingual administration is by placement of the dosage form under the tongue. Buccal and sublingual administration are typically accomplished using a solid oral dosage form, or gel.

Rectal administration may be by administration of a solid oral dosage form, by administration of a semi-solid form such as a suppository, gel, or ointment, by administration of a liquid, or by administration of both a semi-solid and a liquid. Administration of liquids such as solutions, emulsions, dispersions, or combinations thereof may be accomplished with an enema.

A feeding tube may also be used as a route of administration into the alimentary canal.

Parenteral administration includes subcutaneous injection, infusion, or both injection and infusion; intramuscular injection, infusion, or both infusion and injection; intravenous infusion, injection, or both infusion and injection; intra-arterial administration; and other forms of injection and infusion. Intravenous injection or infusion is administration directly into a vein. Subcutaneous injection is injection of into the subcutis, which is the area below the dermis and epidermis of the skin. Intramuscular injection is an injection directly into the muscle. Intra-arterial administration is administration directly to an artery. Examples of compositions for injection and infusion include, without limitation, sterile aqueous or nonaqueous solutions, dispersions, suspensions, and emulsions. Also solutions, suspensions, dispersions, emulsions, and combinations thereof for injection and infusion may be formed from reconstitution of sterile powders.

Although the term "parenterally" may typically be thought of as referring to injection of a drug, or infusion of a drug within the body, the broad definition also encompasses administration by other routes, such as and without limitation, through the skin (transdermal), through the mucosa (transmucosal), for example the mucosa of the nose or the lungs, and injection or insertion into other organs such as without limitation the heart (intracadiac), the vagina (intravaginal), the uterus (intrauterine), the base of the penis (intracaverous injection), the spinal canal (intrathecal), the peritoneum (intraperitoneal), the eye (intravitreal), the bone marrow (intraosseous infusion), and the bladder (intravesical).

Drugs may be administered locally or systemically. Systemic delivery involves the administration of a drug at a discrete location followed by the dispersal of the drug throughout the patient's body including, of course, to the target treatment site or organ. Local delivery comprises administration of the drug in such a manner as to avoid or substantially limit the dispersion of the drug throughout the body. Local delivery instead delivers or concentrates the drug at the target treatment site or in the target organ, such as, for example and without limitation, administration directly to the target site. Drugs may be administered topically for a local effect, such as by direct application of a gel, cream, or ointment to the skin, or application of drops to the eye. In contrast to topical administration, drugs delivered transdermally are intended to have a systemic effect as opposed to only a local effect. Likewise buccal or sublingual administration may result in systemic delivery, may have a local effect, or both.

Transdermal and topical administration may be by means of a semi-solid vehicle such as, without limitation, an ointment, a gel, or a cream, by means of a powder, by means of drops or by means of a transdermal patch. Administration to the mucosa of the lungs or the nasal cavities and sinuses may be by a spray of a liquid, or a suspension, or by the direct application of a powder.

As used herein, the "therapeutic range" of a drug is the range of the plasma concentration of a drug that is safe, that is with minimal side effects, minimal toxicity, or both minimal side effect and toxicity while being effective in most patients. The plasma concentration may be the average plasma concentration, that is the time averaged concentration over 24 hours when the drug is administered as intended, or the plasma concentration may refer to the peak or trough plasma concentration. As used herein, the plasma concentrations for the therapeutic range are steady-state plasma concentrations as opposed to plasma concentrations obtained after a single dose.

As used herein, a "vascular disease" generally refers to a disease, condition, or disorder' that impacts the circulatory system, a system of blood vessels, primarily arteries and veins, which transport blood to and from the heart, brain and peripheral organs such as, without limitation, the arms, legs, kidneys and liver. In particular "vascular disease" refers to the coronary arterial system, the carotid arterial system and the peripheral arterial system.

As used herein, a "cardiovascular disease" is a disease, condition, or disorder that impacts the heart, circulatory system, or both the heart and the circulatory system.

Examples of vascular diseases include, without limitation, atherosclerosis, thrombosis, restenosis, hemorrhage, vascular dissection or perforation, vascular aneurysm, vulnerable plaque, chronic total occlusion, claudication, and anastomotic proliferation for vein and artificial grafts.

"Atherosclerosis" refers to the depositing of fatty substances, cholesterol, cellular waste products, calcium and fibrin on the inner lining, or intima, of an artery. Smooth muscle cell proliferation and lipid accumulation accompany the deposition process. In addition, inflammatory substances that tend to migrate to atherosclerotic regions of an artery are thought to exacerbate the condition as well as increase the production of proinflammatory signals to the cells within the atherosclerotic region. The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting is strokes, if the afflicted artery is a carotid artery, heart attack if the artery is a coronary artery, or loss of organ function if the artery is peripheral.

"Restenosis" refers to the re-narrowing or blockage of an artery at or near the site where angioplasty or another surgical procedure was previously performed to remove a stenosis. It is generally due to smooth muscle cell proliferation at times accompanied by thrombosis. Prior to the advent of implantable stents to maintain the patency of vessels opened by angioplasty, restenosis was due primarily to thrombosis or blood-clotting at the site of the procedure. While the use of IIb-IIIa anti-platelet drugs such as abciximab and epifabatide, which are anti-thrombotic, reduced the occurrence of post-procedure clotting and stents reduced it even further (although stent placement itself can initiate thrombosis), stent placement sites are also susceptible to restenosis due to abnormal tissue growth at the site of implantation. This form of restenosis tends also to occur at 3 to 6 months after stent placement but it is not affected by the use of anti-clotting drugs.

"Vulnerable plaque" refers to an atheromatous plaque that has the potential of causing a thrombotic event and is usually characterized by a very thin wall separating it from the lumen of an artery. The thinness of the wall renders the plaque susceptible to rupture. The walls are formed from collagen which may be negatively impacted by inflammation as well as other substances present in the blood stream. When the plaque ruptures, the inner core of usually lipid-rich plaque is exposed to blood, with the potential of causing a fatal thrombotic event through adhesion and activation of platelets and plasma proteins to components of the exposed plaque.

Peripheral vascular diseases are generally caused by structural changes in blood vessels caused by such conditions as inflammation and tissue damage. A subset of peripheral vascular disease is peripheral artery disease (PAD). PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to the kidneys, stomach, arms, legs and feet.

Vascular regions or sites that may benefit from treatment include, without limitation, atherosclerotic lesions, site of vulnerable plaque(s), and the site of a peripheral arterial disease. An atherosclerotic lesion refers to a deposit of fatty substances, cholesterol, cellular waste products, calcium, fibrin, or a combination thereof on the inner lining or intima of an artery. Examples of vascular lesions include, without limitation, saphenous vein graft lesions, restenotic lesions, bifurcation lesions, ostial lesions, left main lesions, chronic total occlusions and occlusions associated with AMI (Acute Myocardial Infarction), and STEMI (ST-segment Elevation Myocardial Infarction).

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators; cochlear implants; prostheses; vascular grafts; self-expandable stents; balloon-expandable stents; stent-grafts; grafts; artificial heart valves; foramen ovale closure devices; cerebrospinal fluid shunts; and intrauterine devices.

One type of implantable medical device is a stent. Stents are implantable medical devices that are generally cylindrically shaped, and function to hold open, and sometimes expand, a segment of a blood vessel or other lumen or vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease. A stent can be used in, without limitation, neuro, carotid, coronary, pulmonary, renal, biliary, iliac, femoral and popliteal, as well as other peripheral, vasculatures, and in other bodily lumens such as the urethra or bile duct. A stent can be used in the treatment or prevention of vascular disorders such as, without limitation, those described above, as well as other disorders, non-limiting examples of which are bile duct obstruction and ureter obstruction.

Another category of medical devices are insertable medical devices. "Insertable medical devices" include any type of appliance that is totally or partly introduced, surgically or medically, into a patient's body or by medical intervention into a natural orifice, but the device does not remain in the patient's body after the procedure.

A "vascular catheter" is an example of an insertable medical device. A vascular catheter is a thin, flexible tube with a manipulating means at one end, which remains outside the patient's body, and an operative device at or near the other end, which is inserted into the patient's artery or vein. The catheter may be used for the introduction of fluids, often containing drugs, to the target site. The catheter may be used to deliver a stent to the target site, or may be used to deliver a balloon used in angioplasty. The catheter may have multiple functions.

As used herein, a "balloon" refers to the well-known in the art device, usually associated with a vascular catheter, that comprises a relatively thin, flexible material, forming a tubular membrane, that when positioned at a particular location in a patient's vessel can be expanded or inflated to an outside diameter that is essentially the same as the inside or luminal diameter of the vessel in which it is placed. Balloons may be inflated, without limitation, using a liquid medium such as water or normal saline solution, that is, saline that is essentially isotonic with blood.

A "balloon catheter" refers to medical device which is system of a catheter with a balloon at the end of the catheter.

An "introducer sheath" is a tube inserted into the body and allows access of other instruments into parts of the body such as the trachea, a vein, or an artery.

Figure 1:
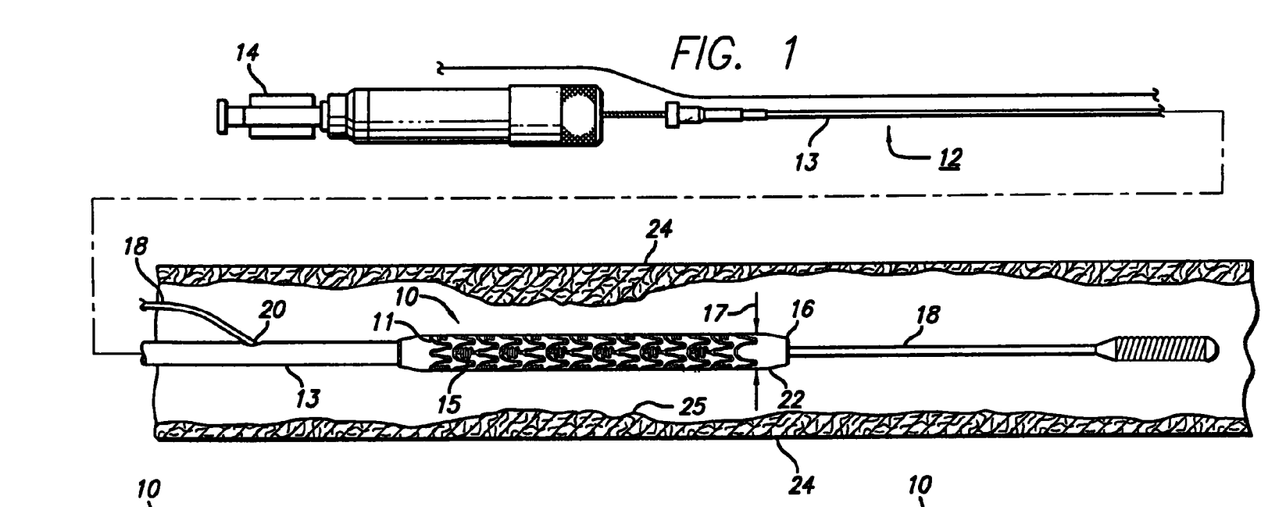
FIG. 1 is an elevational view, partially in section, of a typical stent mounted on a delivery catheter and disposed within a damaged artery.

A typical implantation of a stent is described in the following paragraphs. FIG. 1 generally depicts a stent 10, mounted on a catheter assembly 12 which is used to deliver the stent and implant it in a body lumen, such as a blood vessel. The non-limiting example of a stent that is shown in FIG. 1 comprises a plurality of radially expandable cylindrical rings 11 disposed generally coaxially and interconnected by undulating links 15 disposed between adjacent cylindrical elements. The combination of cylindrical rings and links form the stent body, or scaffolding, which supports the vessel once deployed. The catheter assembly includes a catheter shaft 13 which has two ends, a first end 14 and a second end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well-known rapid exchange type which includes an RX port 20 where the guide wire 18 will exit the catheter from a lumen, which is a passageway or cavity, in the shaft. The distal end of the guide wire 18 exits the catheter second end 16 so that the catheter advances along the guide wire on a section of the catheter between the RX port 20 and the catheter second end 16. If the stent is of the balloon-expandable type, the stent is mounted on the balloon 22 and is crimped tightly thereon so that the stent and balloon present a low profile diameter for delivery through the arteries. Alternatively, a self-expanding stent configuration as is well known in the art may be used.

Figure 2:
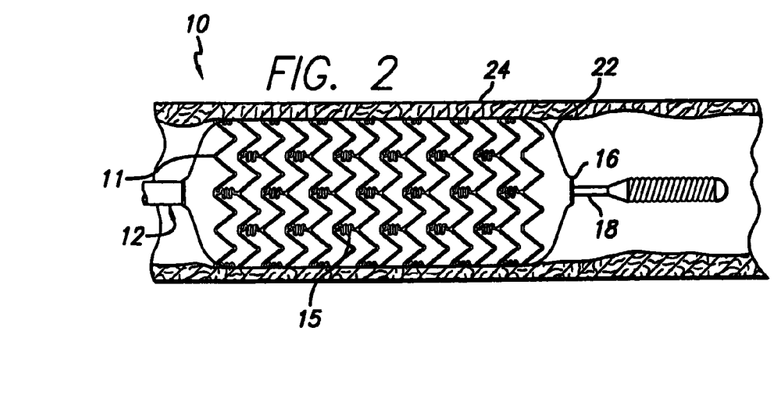
FIG. 2 is an elevational view, partially in section, similar to that shown in FIG. 1 wherein the stent is expanded within a damaged artery.
Figure 3:
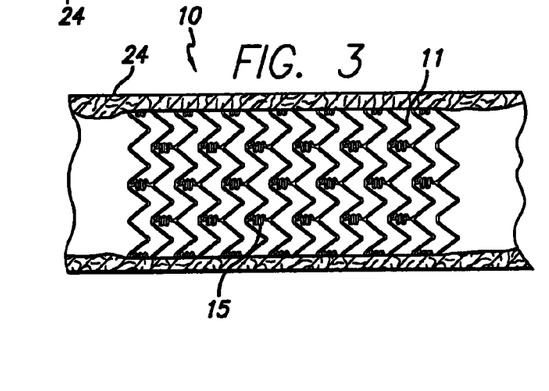
FIG. 3 is an elevational view, partially in section, depicting the expanded stent within the artery after withdrawal of the delivery catheter.

As shown in FIG. 1, a partial cross-section of an artery 24 is shown with a small amount of plaque that has been previously treated by an angioplasty or other repair procedure. A stent 10 is used to repair a diseased or damaged arterial wall which may include the plaque 25 as shown in FIG. 1, or a dissection, or a flap which are commonly found in the coronary arteries, carotid arteries, peripheral arteries and other vessels. In a typical procedure to implant stent 10, the guide wire 18 is advanced through the patient's vascular system by well known methods so that the distal end of the guide wire is advanced past the plaque or diseased area 25. Thereafter, the stent delivery catheter assembly 12 is advanced over the guide wire so that the stent is positioned in the target area. The balloon 22 is inflated by well known means so that it expands radially outwardly and in turn expands the stent radially outwardly until the scent is apposed to the vessel wall. The balloon is then deflated and the catheter withdrawn from the patient's vascular system. The guide wire typically is left in the lumen for post-dilatation procedures, if any, and subsequently is withdrawn from the patient's vascular system. After removal of the guidewire, the lumen in the catheter shaft may be used to deliver fluids, potentially including a drug, to the site. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

A balloon, a catheter, and a stent perform different functions. A stent is crimped to a smaller diameter for delivery, and then the stent subsequently expands if self-expanding, or is expanded by a balloon or other device, to a large diameter. The expanded stent is capable of supporting a bodily lumen for an extended period of time. In contrast, a balloon has a wall thickness that is so thin that the tubular membrane cannot support a load at a given diameter unless inflated with a fluid, such as a liquid or gas. Furthermore, a balloon is a transitory device that is inserted in the patient's body for only a limited time for the purpose of performing a specific procedure or function. Unlike a stent, dilatation balloons are not permanently implanted within the body. Catheters have a shaft which is similar to a stents in that most stents and catheter shafts are tubular or cylindrical in shape. However, a catheter shaft is not designed to be radially expandable.

As discussed previously, the use of stents has reduced the incidence of restenosis, but to a lower extent in diabetic patients. For example, one study found that after a percutaneous cardiac intervention, such as PTCA, followed by the implantation of a bare metal stent, the rate of restenosis was 30% for diabetic patients compared to 20% for non-diabetic patients. Another study involving implantation of a drug-eluting stent (DES), found a rate of 14.6% restenosis in non-diabetics, but 20.9% for diabetic patients. In addition, diabetic patients are more likely to experience major adverse cardiac events (MACE) after PTCA with stenting. In general, diabetics are more than twice as likely as non-diabetics to have a heart attack or stroke, and 2 out of 3 diabetics die from cardiovascular disease (American Diabetes Association). Hyperglycemia, independent of whether or not a person has been diagnosed with diabetes, is a risk-factor for cardiovascular events.

Diabetic patients are those individuals suffering from diabetes mellitus, often referred to as just "diabetes," a group of metabolic diseases. Diabetes may be type 1, previously referred to as juvenile diabetes, in which an individual is unable to produce insulin. Type 1 diabetes may also be called insulin dependent diabetes. Type 2 diabetes results from an insulin level which is too low, or an inability to utilize insulin, referred to as "insulin resistance." A person is diagnosed as diabetic if:
(1) fasting plasma glucose level is greater than or equal to 7.6 mmol/L (126 mg/dL)
(2) plasma glucose level is greater than or equal to 11.0 mmol/L (200 mg/dL) 2 hours after a 75 gram oral glucose load (standard glucose tolerance test)
(3) symptoms of hyperglycemia (described below), and a "casual" plasma glucose of greater than or equal to 11.1 mmol/L
(4) glycated hemoglobin (a.k.a. hemoglobin A1C or HbA1C) of greater than or equal to 6.5%

In general, the measurements should be repeated on more than one day for a definitive diagnosis of diabetes. Hyperglycemia is a condition of high plasma glucose. Symptoms of hyperglycemia include increased thirst and urination, increased hunger, blurred vision, feelings of weakness, weight loss, and dry mouth. Those people with a fasting blood glucose that is 5.6 to 6.9 mmol/liter (100 to 125 mg/dL), or a glucose tolerance test plasma glucose level of 7.8 to 11.1 mmol/liter (140 to 200 mg/dL) are classified as "pre-diabetic."

As used herein, a "diabetic patient" is an individual (animal, including human) who has been diagnosed as having diabetes, either type 1 or type 2, or an individual, although not diagnosed as diabetic, who would meet the clinical definition of a diabetic individual if that individual were to be evaluated. As an example, for a human, if the plasma glucose or HbA1C, if measured, would fall within the range described above that is classified as diabetic, that individual would be classified as a "diabetic patient," even if not formally diagnosed. Different criteria may apply to individuals of different species. The methods of the present invention encompass treatment of those individuals classified as diabetic under current clinical criteria, as well as those who classify as diabetic under any criteria as revised or developed in the future. Those referred to as "pre-diabetic" individuals would be determined analogously.

It is believed that there are a number of reasons that diabetics exhibit higher rates of cardiovascular disease. Diabetics suffer from endothelial dysfunction making diabetics more prone to vascular lesions. The high blood glucose levels may damage heart muscle, and increase oxidative stress. Many diabetic patients have "atherogenic dyslipidemia," or an abnormal lipid profile in the blood. This abnormal lipid profile is characterized by elevated triglycerides, and low levels of high density lipoprotein (HDL) cholesterol. Even if the low density lipoprotein (LDL) cholesterol, also referred to as "bad cholesterol," is at a normal level, the actual LDL particles are often abnormal, such as by being smaller, denser, or both, and as a result, more likely to lead to atherosclerosis. Inflammation also plays a role in the development of diabetes, and plasma levels of inflammatory molecules and adhesion molecules are elevated in diabetic patients. In fact, some have referred to type II diabetes as a "chronic inflammatory disease." At least one study has found a correlation between blood markers of inflammation and the propensity to become diabetic, but the correlation was not applicable to African Americans and smokers. Animal models have shown that T cells and macrophages, both involved in immune response, are involved in the development of diabetes or insulin resistance.

Cardiovascular disease also involves inflammatory processes. It is believed that the atherosclerosis plaque formation initiates with the stimulation of VCAM-1 (vascular cell adhesion molecule-1) by endothelial cells in the wall of the artery. This results in the adhesion of white blood cells, including immune modulated white blood cells. Stimulation of VCAM-1 is thought to occur by oxidized lipids. Another pathway for stimulation of VCAM-1 involves nuclear factor-KB. VCAM-1 may also be stimulated by proinflammatory cytokines, which are small cell-signaling proteins. An example of a proinflammatory cytokine that may stimulate VCAM-1 is IL-1β, interluenkin-1β. VCAM-1 may also be stimulated by a substance called TNF-α, tumor necrosis factor-α. The white blood cells within the vessel wall eventually become macrophages, which are involved in immune response and which engulf and digest cellular debris and pathogens. In the development of atherosclerosis, the macrophages engulf modified lipoproteins in the blood, particularly LDL. In a cascade effect, the macrophages also produce growth factors and cytokines, which are proinflammatory. Eventually the macrophages become the foam cells seen in atherosclerotic plaque.

Stenting and PTCA can injure the vessel wall, such as by causing endothelial denudation, and the injury may cause inflammation. Inflammation may result in changes to smooth muscle cells, with over-proliferations of muscle cells and migration of these cells into the intima. It is the overgrowth of cells that may lead to restenosis. Thus, the vascular injury caused by stenting may eventually lead to restenosis.

Because diabetics suffer from endothelial dysfunction and inflammation, diabetics may be particularly susceptible to restenosis. It is interesting to note that the risk factors for cardiovascular disease and diabetes significantly overlap. Some have gone as far as postulating that both are part of the "metabolic syndrome," that is diabetes and cardiovascular disease, are manifestations of the same underlying disease.

Embodiments of the present invention include methods for the treatment, prevention, or amelioration of vascular disease in diabetic patients where the methods include both implantation of a stent including a first drug. The methods may optionally include additional therapy. In some embodiments, the additional therapy is the administration of a second drug to the patient. The first and the second drugs may be the same, or may be different.

It is believed that restenosis may be prevented, treated, or ameliorated by the administration of an anti-inflammatory, an antibiotic/antimicrobial, or both. It is believed that an anti-inflammatory or antimicrobial combats the inflamed state of the vessel. Other means of preventing, treating, or ameliorating restenosis may be the administration of a drug that interferes with the signaling pathways leading to the accumulation of fatty substances, cholesterol, cellular waste products, calcium and fibrin on the vessel wall. Such drugs include those that reduce the activity of TNF-α, reduce tissue factor activity, or reduce both the activity of TNF-α and tissue factor activity. Drugs which act as anti-coagulants, for example by reducing thrombin activity, as well as drugs reducing platelet activation may also inhibit restenosis by eliminating or reducing the propensity of material to coagulate, to adhere to the vessel wall, or both.

At least one clinical study involving implantation of DES showed a correlation between one inflammatory marker, high sensitive C reactive protein (CRP), in the blood of diabetic patients and rates of restenosis. Another study which involved implantation of bare metal stents, showed no correlation with a large number of inflammatory markers and rates of restenosis. However, both of the above referenced studies concluded that control of diabetes, as determined by HbA1C, plasma glucose, or both, was a factor in the rate of restenosis. Moreover, the study utilizing bare metal stents found that the fasting blood glucose level at the time of stenting correlated with the rate of restenosis. Thus, administration of drugs that improve the responsiveness of the artery to insulin, reduce fluctuation in HbA1C, or both may also be advantageous.

In the various embodiments of the present invention, the first drug included with the stent may be an anti-inflammatory, an antiproliferative, an antineoplastic, an antimitotic, an antiplatelet, an anticoagulant, an antifibrin, an antithrombin, antibiotic, an anti-allergic, an antioxidant substance, or any combination thereof, where combination encompasses combinations of two or more of drugs are in the same category, optionally with a drug from another category (for example, two antiproliferatives, or as another example, two anti-inflammatories, and an anti-coagulant). As used herein, the administration of an "antioxidant" refers to administration of antioxidants that are administered to individuals for a therapeutic benefit. In other words, "administration of an antioxidant" does not encompass administration of a formulation or use of a device which incidentally includes antioxidants used as additives to stabilize a drug or a formulation, unless these antioxidants are also commonly administered to patients as a drug and are present at a therapeutically effective level. As an example, the antioxidants butylated hydroxytoluene and butylated hydroxyanisole are often used to stabilize drug formulations, and thus their presence in a drug formulation would not necessarily be to provide a therapeutically beneficial effect for the patient. On the other hand, some antioxidants, such as Vitamin E, may be administered to individuals as a drug, but may also be used to stabilize a drug formulation.

The stent comprising the first drug may be of any type of drug eluting stent. Examples include, without limitation, stents with holes, grooves, pores, indentations, or a combination thereof in the surface where the drug is partially or completely contained within at least a portion of the holes, grooves, pores, indentations or combinations thereof; porous or hollow stents where the drug may be contained within the pores or within the hollow interior of the stent; and stents in which the drug may be coated on the exterior. The exterior coating may include only a drug, or the exterior coating may include a drug in combination with another material such as a polymer, a metal, a metal alloy, a ceramic, a glass, or any combination thereof. The coating may be constructed of multiple layers, the coating may be applied as multiple layers, or both. Multiple layers may have different materials, different ratios of materials, or both in each layer.

The stent may be a bioabsorbable stent where the first drug is included in the body or scaffolding of the stent. As an example, the stent may be a bioabsorbable polymeric stent the drug is dispersed within the polymeric scaffolding of the stent.

Porous or hollow stents, stents with grooves, holes, indentations, pores or a combination thereof, and bioabsorbable stents may be coated or uncoated. The stent coating, if present, may be formed from a polymer, a metal, a metal alloy, a ceramic, a glass, and any combination thereof. The stent coating may or may not include the first drug. The stent coating may or may not include an additional drug. A bioabsorbable stent may be coated with a drug containing coating instead of or in addition to having drug incorporated into the scaffolding of the bioabsorbable stent. The stent may include any consistent combination of the above features. For example, that is the stent may be a bioabsorbable porous or hollow stent with an exterior coating, which may or may not include the first drug, an additional drug, or both.

The stent may be of any design. The stent may be a self-expanding stent, or a balloon expandable stent. The stent may be formed from a polymer, a metal, a metal alloy, a ceramic, a glass, and any combination thereof. The stent may be made from biostable materials, biodegradable materials, or any combination of biostable, and biodegradable materials.

The second drug may reduce inflammation, reduce the amount, the activity, or both the amount and the activity of tumor necrosis factor alpha, improve the responsiveness of the artery to insulin, reduce platelet activation, reduce fluctuation in hemoglobin A1C, reduce tissue factor activity, reduce thrombin activity, or any combination of these.

The second drug may be administered over a definite time period. A definite time period has a clearly defined beginning and end. Most diabetics take medication to control blood glucose, and may optionally take other medication, such as high blood pressure medication. These examples are examples of medications for the treatment of a chronic condition, and the medication is prescribed with the expectation that the patient will be on the medication for the duration of their lifetime. As used herein, medications taken for chronic conditions are not administered for a definite time period as there is no clearly defined time point at which the administration of the medication ends.

It is believed that the administration of a second drug, a food supplement (described below) or both, optionally in conjunction with other aspects of stent design that are described below, may improve the rate of restenosis. It is also believed that embodiments of the present invention may reduce the severity, rate, or both the severity and the rate of major adverse cardiac events for diabetic patients who have undergone PTCA and stenting. It is believed that additional therapy, medication, or both additional therapy and medication, used in addition to any medication that the patient is currently taking may address some of the root causes of restenosis, cardiovascular disease, or both in diabetic patients.

In some embodiments, the second drug is administered orally or transdermally. When administered orally, transdermally, or both orally and transdermally, the definite time period of administration of the second drug may begin at least at the time of implanting the stent, at least 1 day, 1 day, about 1 day, 1 day to 3 days, about 1 day to about 3 days, at least 7 days, about 7 days to about 14 days, 7 days to 14 days, at least 14 days, 14 days to 21 days, about 14 days to about 21 days, 10 days to 18 days, about 10 days to about 18 days, at least 8 hours, about 8 hours, 8 hours, 8 hours to 16 hours, about 8 hours to about 16 hours, about 4 hours to about 8 hours, at least 4 hours, 4 to 8 hours, about 4 hours to about 6 hours, 4 to 6 hours, 4 hours to 12 hours, about 4 hours to about 12 hours, about 30 minutes, or at least 30 minutes prior to implantation, or within 30 minutes to 90 minutes, or within about 2 hours of implantation. When administered orally, transdermally, or both orally and transdermally, the definite time period of the administration of the second drug may end at least 1 week, 1 week to 2 weeks, about 1 week to about 2 weeks, 1 week to 3 weeks, about 1 week to about 3 weeks, 2 weeks to 4 weeks, about 2 weeks to about 4 weeks, at least 2 months, about 2 months, about 1 month to about 2 months, 1 to 2 months, 1 to 3 months, about 1 month to about 3 months, at least 3 months, about 3 months to about 6 months, 3 months to 6 months, 3 months to 4 months, about 3 months to about 4 months, at least 6 months, about 6 month to about 9 months, 6 months to 9 months, about 6 months, at least 9 months, about 9 months, about 9 months to about 12 months, 9 months to 12 months, about 9 months to about 18 months, 9 months to 18 months, 12 to 18 months, about 12 months to about 18 months, 15 months to 18 months, or about 15 months to about 18 months after implantation. Embodiments of the present invention encompass oral administration, transdermal administration, or both oral and transdermal administration of the second drug over at least the definite periods determined by the combinations of the above cited beginning and ending times.

In some embodiments, the second drug is administered by subcutaneous injection, intravenous injection, intravenous infusion, or a combination thereof. When administered by subcutaneous injection, intravenous injection, intravenous infusion, or a combination thereof, the definite time period of the administration of the second drug may begin immediately prior to or at the time of implanting the stent, or at least 1 hour prior to implantation, 1 hour prior to implantation, about 1 hour prior to implantation, 1 to 3 hours prior to implantation, about 1 hour to about 3 hours prior to implantation, 2 hours prior to implantation, about 2 hours prior to implantation, 2 to 3 hours prior to implantation, about 2 to about 3 hours prior to implantation, 2 to 4 hours prior to implantation, about 2 to about 4 hours prior to implantation, about 3 hours prior to implantation, about 4 hours prior to implantation, 30 to 90 minutes prior to implantation, 30 to 60 minutes prior to implantation, about 30 to about 90 minutes prior to implantation, about 30 to about 60 minutes prior to implantation, or during the operation. When administered by subcutaneous injection, intravenous injection, intravenous infusion, or a combination thereof, the definite time period of the administration of the second drug may end at about 2 hours after implantation, at 2 hours after implantation, 1 to 4 hours after implantation, about 1 to about 4 hours after implantation, at least 2 hours after implantation, at least 3 hours after implantation, at most 2 hours after implantation, at most 3 hours after implantation, at most 4 hours after implantation, or at most 1 hour after implantation. Embodiments of the present invention encompass administration of the second drug by subcutaneous injection, intravenous injection, or intravenous infusion over definite time periods defined by all of the combinations of the above cited beginning and ending times.

In some embodiments, the second drug is administered intra-arterially. Non-limiting means of intra-arterial administration of the second drug include intra-arterial administration by a catheter, by an introducer, and a combination thereof. When administered intra-arterially, the second drug may be administered prior to the implantation of the stent, that is within 30 minutes, preferably within 20 minutes, and more preferably, within 10 minutes, before the stent is deployed, or when the patient is in the operating room for the operation in which the stent is implanted. In some embodiments, the second drug may be administered intra-arterially 30 to 90 minutes prior to stent implantation or deployment, within 60 minutes prior of stent implantation or deployment, or within 45 minutes prior to stent implantation or deployment. In some embodiments, for intra-arterial administration the drug is administered during the stent implantation, that is during the delivery to the vascular region, during the deployment of the stent, or both during the delivery of the stent to the vascular region and the deployment of the stent, and after the catheter for delivering the stent has been inserted into the body. For intra-arterial administration, the second drug may be administered immediately after implantation of the stent, which is within 10 minutes, preferably within 5 minutes, after the stent is deployed, within 30 minutes after stent deployment, or after stent deployment, but before the removal of the catheter or other delivery device used to implant the stent. In another embodiment, for intra-arterial administration of the second drug, the second drug may be administered after the implantation of the stent and after the removal of the catheter or other delivery device used to implant the stent, such as within 60 minutes or within 30 minutes after the catheter or other device is removed. Intra-arterial administration may occur at up to at most 4 hours after deployment, and preferably, at most 2 hours. For example, and without limitation, a solution or suspension of the drug may be flushed over the vascular region of interest from an introducer or catheter peri-procedurally with the implantation of the stent.

For a time defined as being prior to stent implantation, the time of "stent implantation," that is the time zero from which earlier time points are determined, may be at the time a delivery device with the stent is inserted into the patient, at the time the patient undergoes any pre-operation procedures excluding the administration of the second drug, or the time at which the patient is prepared for the stent implantation. For a time defined as being "after stent implantation," the time zero from which later time points are determined may be the time that catheter or delivery device used to implant the stent is removed from the body, the time the stent is fully expanded, or the time that all post-operation procedures are completed, except administration of the second drug. Embodiments of the present invention encompass at least the definite time periods determined using the above stent implantation times.

"Administration" of the second drug encompasses both continuous administration, as by infusion, administration at specified time points over the time period, or a combination thereof. As an example, oral administration may be administration of a tablet two times per day over the time period, where the first time and last time the tablets are taken represent the beginning and the ending of the time period, respectively. As another example, intravenous administration may be an infusion over a 1 hour time period, and one or more bolus injections or administrations over a short time period such as 1 minute at one or more additional times with the last bolus injection defining the end of the administration period. As another example, intravenous infusion may occur for 15 minutes of each hour over a 4 hour period.

In some embodiments, the second drug is administered orally, transdermally, or a combination thereof, and the second drug is an anti-microbial. In some embodiments, the second drug may be a thiazolidinedione (a.k.a. a glitazone) such as, but without limitation, troglitazone, rosiglitazone, and pioglitazone, and may be administered orally, transdermally, or both orally and transdermally. At least one study of limited size has demonstrated a reduction in the rate of restenosis after implantation of a bare metal stent for diabetic patients who were prescribed rosiglitzone as compared to the control group. A bare metal stent is a stent with scaffolding constructed of a metal or a metal alloy, and which has no coating. The second drug may be an anti-platelet, a thrombin inhibitor, an anti-coagulant, or a combination thereof, such as without limitation cilotostzol, presugrel, tigacrelor, or a combination thereof, and may be administered orally. The second drug may be an anti-IL-6, and may be administered orally. The second drug may be an anti-TNF-α, and may be administered transdermally.

In some embodiments, the second drug is an anti-microbial and is administered intravenously. In some embodiments, the second drug is adalimumab and is administered subcutaneously. In some embodiments, adalimumab is administered subcutaneously at least at 2 hours or at about 2 hours prior to the stent deployment, during stent deployment, at 2 hours or at about 2 hours after stent deployment, or any combination thereof.

In some embodiments, the second drug is administered orally, transdermally, or both orally and transdermally, and the second drug is administered at a dose, such that the plasma concentration is lower than the lower end of the therapeutic range for normal use. The therapeutic range for normal use is the therapeutic range obtained at steady-state when the drug is administered as monotherapy as indicated on the label, on the package insert, or both the label and the package insert for the primary approved indication of the drug, or if off-label use is prevalent, the therapeutic range obtained at steady-state for the typical dosing schedule for the off-label use. Approved indications are those approved by the United States Food and Drug Administration (FDA) at the time of the filing of the present application. The primary approved indication may be that which was first approved by the FDA, that indication which is most prescribed, or it may be a combination of both.

The second drug may be administered orally, transdermally, or a combination of orally and transdermally, in one or more cycles. A cycle includes administration at a higher first dose, and then at least 1 additional subsequent administration at a second lower dose. In some embodiments, the first higher dose is a dose for which the plasma concentration is within the therapeutic range for normal use, or the first higher dose is a dose for which the steady-state plasma concentration would be within the therapeutic range for normal use if steady-state at the dose were to be attained, and the second lower dose is a dose for which the plasma concentration is below the lower limit of the therapeutic range for normal use, or the second lower dose is a dose for which the steady-state plasma concentration would be below the lower limit of the therapeutic range for normal use. In other embodiments, the first higher dose would be an effective dose for the particular patient for the primary indication or prevalent off-use indication, and the second dose would be substantially lower than the first dose, such as at least 20% lower, at least 30% lower, or at least 50% lower than the first dose, and the second dose would also be lower than the lower end of the therapeutic range for normal use. In still other embodiments, the second dose may be substantially lower than the first dose, such as at least 20% lower, at least 30% lower, or at least 50% lower, than the first higher dose. There may be multiple lower doses or a series of step-downs in dosage to a final lower dose.

The second lower dose may be a dose such that the average plasma concentration may be at most 90%, 80% to 90%, about 80% to about 90%, 70% to 85%, about 70% to about 85%, 50% to 85%, about 50% to about 85%, 40% to 80%, about 40% to about 80%, 65% to 80%, about 65% to about 80%, 40% to 75%, about 40% to about 75%, 55% to 75%, about 55% to about 75%, 25% to 70%, about 25% to about 70%, 50% to 70%, about 40% to about 70%, 50% to 70%, about 50% to about 70%, 20% to 60%, about 20% to about 60%, 25% to 50%, about 25% to about 50%, 25% to 35%, about 25% to about 35%, or less than 25% of the lower limit of the therapeutic range, where the plasma concentration range in the therapeutic range may be expressed as an average concentration, a peak concentration, a trough concentration, or a concentration at a specific point in time relative to the dosing as determined at steady-state.

The ratio of the time during the cycle in which the higher dose is administered to the time during which the lower dose(s) are administered may be in the range from 8:1 to 1:8, preferably from 4:1 to 1:4, and in some embodiments may be in the range from 2:1 to 1:2. In some embodiments the ratio may be about 1:1 or 1:1.

The ratio of the time during the cycle in which the plasma concentration is within the therapeutic range for normal use to the time during the cycle in which the plasma concentration is below the lower end of the therapeutic range for normal use may be in the range from 8:1 to 1:8, preferably from 4:1 to 1:4, and in some embodiments may be in the range from 2:1 to 1:2. In some embodiments the ratio may be about 1:1 or 1:1.

In some embodiments, there are multiple cycles, such as and without limitation, 2 cycles, 3 cycles, 4 cycles, 5 cycles, at least 2 cycles, at least 3 cycles, at least 4 cycles, or at least 5 cycles. The administration may occur over any of the definite time periods described previously.

If there is more than 1 cycle of administration, the duration of each cycle may be the same or different from the duration of any other cycles. The ratio of the time of administration of the high dose to the time of administration of the low dose may be the same or different for each of multiple cycles. In some embodiments, the actual "high" dose and "low dose" may vary from cycle to cycle.

In some preferred embodiments of the invention, the stent including a first drug is a stent having a scaffolding that is metallic, with the first drug included in a polymeric coating which is disposed over at least a portion of the exterior surface of the stent, or substantially all of the exterior surface of the stent, and the first drug is everolimus, zotarolimus, rapamycin, or a combination thereof, and the coating includes a fluoropolymer. In alternative preferred embodiments, the stent is a bioabsorbable polymeric stent with a scaffolding made substantially of a polymer, preferably poly(L-lactide), poly(L-lactide-co-glycolide), or a combination thereof, with the drug being included in a polymeric coating disposed over at least a portion of the exterior surface of the stent, or substantially all of the exterior surface of the stent, and the drug being everolimus, zotarolimus, rapamycin, or a combination thereof, and the coating including poly(D,L-lactide).

In some preferred embodiments, the second drug may be doxycline (such as, without limitation, doxycycline hyclate) that is administered orally at a dose such that the steady-state plasma concentration is below the lower limit of the therapeutic range, the administration beginning at 7 days or about 7 days prior to implantation of the stent, and the administration ending at 1 month post stent implantation. In alternative embodiments, the doxycycline may be administered intravenously beginning at about 2 hours prior to implantation, continuing throughout implantation, and ending at about 2 hours after implantation, where the administration may be continuous or intermittent. In other alternative embodiments, the doxycline may be administered intravenously via at least one bolus injection at 2 hours prior to implantation, or about 2 hours prior to implantation, at least one bolus injection during the procedure, and at least one bolus injection at 2 hours or at about 2 hours after implantation of the stent, the time point at which the intravenous administration of the doxycline ends. In some embodiments, both oral doxycline and intravenous doxycline may be administered.

In other preferred embodiments, adalimumab is administered as a subcutaneous injection according to the recommendation of the current package insert. In alternative preferred embodiments, the adalimumab may be administered via subcutaneous injection at a lower does than currently recommended in the package insert such that the steady-state plasma concentration is lower than the lower end of the therapeutic range. In yet other alternative embodiments, the dose of adalimumab is cycled between a higher dose and a lower dose. The higher dose of adalimumab may be selected to result in a plasma concentration that is within the therapeutic range or may be selected such that the steady-state plasma concentration would be within the therapeutic range if steady-state were attained. The lower dose may be selected to result in a plasma concentration that is lower than the lower end of the therapeutic range, or it may be selected such that the steady-state plasma concentration would be below the lower end of the therapeutic range if steady-state were attained. In some embodiments, the lower dose, whether administration is by cycling the dose or no cycling, is selected such that the plasma concentration is 20% to 80% of the lower limit, 40% to 60% of the lower limit, or 30% to 75% of the lower limit of the therapeutic range.

In other preferred embodiments, instead of, or in addition to doxycline, an oral glitazone is administered beginning at 7 days, at about 7 days prior to the implantation of the stent, and ending at about 1 month, at 1 month after implantation, or at about 2 months after implantation. In other preferred embodiments, a glitazone is administered via a transdermal patch, and administration begins at 7 days, or at about 7 days prior to the implantation of the stent, and ends at about 1 month, or at 1 month after implantation.

In still other preferred embodiments, a drug which is an anti-TNF biologic, such as an anti-TNF-α biologic, is administered by subcutaneous injection or implantation. The administration of the anti-TNF may begin at 7 days, at about 7 days, at 2 days, at about 2 days, at 24 hours, at 24 hours, within 24 hours, or within 6 hours prior to the implantation of the stent, and may end at about 1 month, at 1 month, at 2 months, or at about 2 months after implantation. The injection/implantation may be of gel, which may be made from, at least in part, hyaluronic acid, and may also include vesicles. A vesicle refers to sack, cavity or pouch, typically filled with a liquid or gas. As used herein a "vesicle" is a compartment completely enclosed by a layer of material, or membrane that separates the compartment and whatever may be contained in it from the external environment. The membrane is the "outer shell" of the vesicle, and the material inside is the "core." The core may be filled with a fluid, such as a liquid, or a gel, or semi-solid. A vesicle may be of any shape or no shape, i.e., essentially amorphous. Generally, however, vesicles tend to be substantially spherical or ovoid in shape. For a biological vesicle, the membrane may be formed from lipids. Vesicles created may be formed from naturally occurring lipids or phosopholipids which self-assemble into a bilayer, block copolymers, or a combination thereof.

In other preferred embodiments, the second drug may be insulin, and in a more preferred embodiment, insulin with a long half-life. Insulin is typically administered by sub-cutaneous injection. The insulin administration may begin on the day of the stent implantation, or 2 to 3 days before the day of stent implantation, and may end at a month or about a month, about 2 to about 4 months, about 2 months to about 3 months, about 3 months to about 6 months, about 4 months to about 8 months, or about 4 months to about 6 months after stent implantation.

In other preferred embodiments, the second drug is cilostazol, a drug exhibiting with both vasodilatory and antithrombotic effects, while in still other preferred embodiments, the second drug is presugrel, tigacrelor, or a combination thereof. The time period for the administration may be any of those disclosed herein.

Embodiments of the present invention include methods for the treatment, prevention, or amelioration of vascular disease in diabetic patients where the methods include the implantation of a stent, where the stent, whether a bare metal stent or a drug eluting stent, is greater in length in both. In other words, the stent length would be determined as is typically done, and then for the diabetic patient, a stent would be selected which is about 2 mm to about 8 mm, about 3 mm to about 7 mm, about 4 mm to about 6 mm, or about 5 mm, or 5 mm greater in length in both directions. In alternative embodiments, instead of or in addition to a longer stent, the stent design may be such that the surface area at the edges or ends is greater. A larger surface area would prevent or decrease the amount of shifting of the stent, as well as also carry more drugs, if a DES and assuming the drug per unit surface area is constant or essentially constant. In some embodiments, the surface area is about 5% to about 50% greater, about 10% to about 40%, or about 15% to about 30% greater on the ends than that determined at the mid-point or within the length representing the middle 40% to 60% of the stent length. In some embodiments, the "end" of the stent is about 5 to 15% of the length at each end. In some embodiments, the "end" is about 3% or less of each end of the stent. In some embodiments, there is a gradation in surface area such that the end has higher surface area than the middle. A higher surface area at the edges than in the middle of the stent may be obtained by increasing the number of struts per unit length at the ends of the stent for example at least 10% more, at least 20% more, or about 10% to about 50% more struts at the end compared to the middle; by increasing the area per strut at the ends compared to the middle, such as at least 10% greater surface area, at least 20% greater surface area, at least 30% greater surface area, or about 10% to 50% greater surface area for the struts at the end compared to the middle. Other means for increasing the surface area at the ends as compared to the middle of the stent may be used.

Non-limiting examples of drugs that may be used in any of the embodiments of the present invention are provided below. The drugs may be used individually or in combination, including combinations of two or more drugs from the same category. Some drugs may belong to more than one category.

Examples of antiproliferative drugs, cytostatic drugs, or both include, without limitation, actinomycins, taxol, docetaxel, paclitaxel, sirolimus (rapamycin), biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxyl)ethyl-rapamycin (everolimus), 40-O-(3-hydroxypropyl)rapamycin, 40-O-[2-(2-hydroxy)-ethoxy]ethyl-rapamycin, 40-O-tetrazole-rapamycin, 40-O-tetrazolylrapamycin, 40-epi-(N1-tetrazole)-rapamycin, and suramin.

Examples of antineoplastics, antimitotics, or both, include, without limitation, paclitaxel, docetaxel, methotrexate, azathioprine, vincristine, vinblastine, fluorouracil, doxorubicin hydrochloride, and mitomycin.

A non-limiting example of a drug that reduces the activity, the amount, or both the activity and the amount of TNF-α is adalimumab.

Examples of anti-platelet, anticoagulant, antifibrin, and antithrombin drugs include without limitation, heparin, sodium heparin, low molecular weight heparins, heparinoids, hirudin, argatroban, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin, from Biogen), prostaglandin inhibitors, phosphodiesterase inhibitors, cilotazol, prasugrel, and tigacrelor.

Other drugs which may have a positive effect on vascular or cardiovascular disease include calcium channel blockers such as nifedipine, colchicine, fish oil (omega 3-fatty acid), angiotensin converting enzyme inhibitors (ACE inhibitors), forskolin, histamine antagonists, statins, monoclonal antibodies such as those specific for Platelet-Derived Growth Factor (PDGF) receptors, nitroprusside, steroids, thioprotease inhibitors, triazolopyrimidine, serotonin blockers, nitric oxide or nitric oxide donors, super oxide dismutases, super oxide dismutase mimetic, and 4-amino-2,2,6,6-tetramethylpiperidine-1-oxyl (4-amino-TEMPO).

Examples of ACE inhibitors include, without limitation, quinapril, perindopril, ramipril, captopril, benazepril, trandolapril, fosinopril, lisinopril, moexipril, and enalapril.

Statins are a class of drugs that can reduce LDLs by means of blocking an enzyme in the liver used to manufacture cholesterol. Non-limiting examples of statins are lovastatin, simvastatin, atorvastatin, fluvastatin, pravastatin, and rosuvastatin.

Angiotensin II receptor blockers (ARBs), which are used to treat high blood pressure (a.k.a hypertension) and heart failure, also show anti-inflammatory properties, and thus, may be used as the first, the second drug, an additional drug, or any combination of these in the embodiments of the invention. Examples of angiotensin II receptor antagonists include, without limitation, irbesartan and losartan.

Examples of anti-inflammatory drugs include both steroidal and nonsteroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopro­fen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, tacrolimus and pimecrolimus.

Examples of steroidal anti-inflammatory drugs include, without limitation, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

Examples of nonsteroidal anti-inflammatory drugs include, without limitation, COX-1 and COX nonspecific inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin), and selective COX-2 inhibitors (e.g., diaryl-substituted furanones such as rofecoxib; diaryl-substituted pyrazoles such as celecoxib; indole acetic acids such as etodolac and sulfonanilides such as nimesulide), and combinations thereof.

There are several mechanisms by which a drug may reduce fluctuations in HbA1C. One mechanism of action is to increase insulin production, and thus reduce the level of plasma glucose with a concomitant reduction in HbA1C. Non-limiting examples of drugs in this class include saxagliptin and sitagliptin, both of which are dipeptidyl-peptidease 4 (DPP-4) inhibitors, exenatide, which is a glucagon-like peptide-1 agonist, meglitinides such as regaglinide and nateglinide, and sulfonylurea drugs, such glyburide, glimepiride, and glipizide. Other drugs improve the effectiveness of insulin or help the body to better utilize insulin. Non-limiting examples of these drugs include metformin, a biguanide, and repaglinide and natalinide, both of which are thiazolidinediones. Leptin and cinnamon may also increase the effectiveness or responsiveness of tissue to insulin. Some drugs impact the fluctuation of HbA1C by alteration of food absorption which in turns regulates the rate of glucose or carbohydrate introduction into the bloodstream. Acrabose and miglitol are examples of these types of drugs.

Examples of antioxidants include, without limitation, Vitamin E, resveratrol and quercetin.

Anti-infective agents generally include, but are not limited to antibiotics, antibacterial agents, antifungal agents, antiparasitic agents, antiviral agents, and antiseptics. As used herein, "antimicrobials" refers to antibiotics, antibacterial agents, antifungal agents, antiparasitic agents, and antiviral agents.

Examples of antibacterial agents include, but are not limited to, aminoglycosides such as streptomycin and gentamicin; amphenicols, such as chloroamphenicol, florfenicol, and thiamphenicol; ansamycins, such as 17-allyl-aminogeldanamycin (17-AAG); the betalactams, including penicillins, such as amoxicillin, carabpenems, such as cilastin and imipenem, and the cephalosporins, such as cephalexin, cephatolein, and cefaclor; llincosamides, such as clindamycin and clindamycin hydrochloride; macrolides, such as erythromycin, azithromycin and clarithromycin; nitrofurans, such as furazolidone, nitrafurazone, and nitrofurantoin; nitroimidazoles, such as metronidazole, ornidazole, and tinidazole; quinolones, such as ciprofloxacin, levofloxacin, moxifloxacin, and ofloxacin; sulfonamides, such as co-trimoxazole and trimethoprim; sulfones, tetracyclines, such as tetracycline and doxycycline; and glycopeptides antibiotics, such as vancomycin.

Examples of antifungal agents include, but are not limited to, allylamines, imidazoles, polyenes, thiocarbamates, triazoles, and any of their derivatives.

Examples of antiparasitic agents include, but are not limited to, such agents as atovaquone, clindamycin, dapsone, iodoquinol, metronidazole, pentamidine, primaquine, pyrimethamine, sulfadiazine, trimethoprim/sulfamethoxazole, and trimetrexate.

Examples of antiviral agents include, but are not limited to, acyclovir, famciclovir, valacyclovir, edoxudine, ganciclovir, foscamet, cidovir (vistide), vitrasert, formivirsen, HPMPA (9-(3-hydroxy-2-phosphonomethoxypropyl)adenine), PMEA (9-(2-phosphono methoxy ethyl) adenine), HPMPG (9-(3-Hydroxy-2-(Phosphonomet-hoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxamide), LY253963 (1,3,4-thiadiazol-2-yl-cyanamide), RD3-0028 (1,4-dihydro-2,3-Benzodithiin), CL387626 (4,4'-bis[4,6-d].beta.-aminophenyl-N-,N-bis(2-carbamoylethyl)-sulfonilimino]-1,3,5-triazin-2-ylamino-biphenyl-2-,2'-disulfonic acid disodium salt), and BABIM (Bis[5-Amidino-2-benzimidazoly-1]-methane), NIH351.

Example of polymers which may be included, individually or in combination, in a coating on a stent, in the scaffolding of a stent, in the formation of part of a stent, or any combination thereof include, without limitation, poly(N-acetylglucosamine) (chitin), chitosan, poly(3-hydroxyvalerate), poly (lactide-co-glycolide), poly(3-hydroxybutyrate), poly(4-hydroxybutyrate), poly(3-hydroxybutyrate-co-3-hydroxyvalerate), polyorthoesters, polyanhydrides, poly (glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly (glycolide-co-caprolactone), poly(trimethylene carbonate), poly(ester-amide) polymers generally, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose, ethylene vinyl alcohol copolymer (commonly known by the generic name EVOH or by the trade name EVAL™), poly(butyl methacrylate), poly (vinylidene fluoride-co-hexafluoropropene) (e.g., SOLEF 21508™, available from Solvay Solexis PVDF, Thorofare, NJ), polyvinylidene fluoride (otherwise known as KYNAR™, available from ATOFINA Chemicals, Philadelphia, Pa.), ethylene-vinyl acetate copolymers, poly(vinyl acetate), styrene-isobutylene-styrene triblock copolymers, and polyethylene glycol, and combinations thereof.

As used herein, the terms poly(D,L-lactide) (PDLL), poly (L-lactide) (PLL), poly(D,L-lactide-co-glycolide) (PDLLG), and poly(L-lactide-co-glycolide) (PLLG) are used interchangeably with the terms poly(D,L-lactic acid) (PDLLA), poly(L-lactic acid) (PLLA), poly(D,L-lactic acid-co-glycolic acid) (PDLLAGA), and poly(L-lactic acid-co-glycolic acid) (PLLAGA), respectively.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention. Moreover, although individual aspects or features may have been presented with respect to one embodiment, a recitation of an aspect for one embodiment, or the recitation of an aspect in general, is intended to disclose its use in all embodiments in which that aspect or feature can be incorporated without undue experimentation.

What is claimed is:

1. A method of treating, preventing, or ameliorating a vascular disease in a diabetic patient, the method comprising:
   implanting a stent comprising a first drug in a vascular region of a diabetic patient; and
   administering a second drug to the diabetic patient via transdermal administration;
   wherein the first drug is an anti-inflammatory, an antiproliferative, an antineoplastic, an antimitotic, an antiplatelet, an anticoagulant, an antifibrin, an antithrombin, an antibiotic, an anti-allergic, an antioxidant substance, or any combination thereof;
   and
   wherein the second drug reduces platelet activation, reduces tissue factor activity, reduces thrombin activity, or any combination thereof.

2. The method of claim 1, wherein the second drug is administered transdermally over a time period which begins at least at the time of the implantation of the stent and ends at least 1 month after the implantation of the stent.

3. The method of claim 2, wherein the second drug is administered transdermally over a time period which begins at least 7 days prior to the implantation of the stent and ends at least 1 month after the implantation of the stent.

4. The method of claim 3, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

5. The method of claim 2, wherein the time period over which the second drug is administered ends at least 6 months after the implantation of the stent.

6. The method of claim 5, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

7. The method of claim 2, wherein the time period over which the second drug is administered ends at 6 months after the implantation of the stent or at about 6 months after the implantation of the stent.

8. The method of claim 7, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

9. The method of claim 2, wherein the second drug is an anti-TNF biologic.

10. The method of claim 9, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

11. The method of claim 2, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

12. The method of claim 1, wherein the second drug is adalimumab.

13. The method of claim 1, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

14. The method of claim 1, wherein the second drug reduces platelet activation.

15. The method of claim 14, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

16. The method of claim 1, wherein the second drug reduces thrombin activity.

17. The method of claim 16, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

18. The method of claim 1, wherein the second drug reduces tissue factor activity.

19. The method of claim 18, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

20. A method of treating, preventing, or ameliorating a vascular disease in a diabetic patient, the method comprising:
selecting a stent with higher surface area at the edges than in the middle of the stent, selecting a stent of a length that is 5 mm longer at each end than the length that would be selected for a non-diabetic patient, or selecting a stent with higher surface area at the edges than in the middle of the stent that is of a length that is 5 mm longer at each end than the length that would be selected for a non-diabetic patient;
wherein the selected stent comprises a first drug; and
implanting the selected stent comprising the first drug in a vascular region of a diabetic patient.

21. The method of claim 20, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

22. The method of claim 20, wherein the selected stent is of a length that is 5 mm longer at each end than the length that would be selected for a non-diabetic patient.

23. The method of claim 20, wherein the selected stent is of higher surface area at the edges than in the middle of the stent and is of a length that is 5 mm longer at each end than the length that would be selected for a non-diabetic patient.

24. A method of treating, preventing, or ameliorating a vascular disease in a diabetic patient, the method comprising:
implanting a stent comprising a first drug in a vascular region of a diabetic patient; and
administering a second drug to the diabetic patient;
wherein the first drug is an anti-inflammatory, an antiproliferative, an antineoplastic, an antimitotic, an antiplatelet, an anticoagulant, an antifibrin, an antithrombin, an antibiotic, an anti-allergic, an antioxidant substance, or any combination thereof;
wherein the second drug reduces inflammation, reduces the amount, the activity, or both the amount and the activity of tumor necrosis factor alpha, improves the responsiveness of the artery to insulin, reduces platelet activation, reduces fluctuation in hemoglobin A1C, reduces tissue factor activity, reduces thrombin activity, or any combination thereof;
and
wherein
the second drug is administered in one or more cycles, each cycle comprising administration at a first dose such that the plasma concentration is within therapeutic index for normal use and then a subsequent administration at a second lower dose such that the plasma concentration is below the therapeutic index for normal use.

25. The method of claim 24, wherein
the second drug is administered by subcutaneous or intravenous injection over a time period beginning at least 2 hours prior to the implantation of the stent and continuing to at least 2 hours post-implantation of the stent.

26. The method of claim 25, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

27. The method of claim 24, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

28. A method of treating, preventing, or ameliorating a vascular disease in a diabetic patient, the method comprising:
implanting a stent comprising a first drug in a vascular region of a diabetic patient; and
administering a second drug to the diabetic patient via an introducer;
wherein the first drug is an anti-inflammatory, an antiproliferative, an antineoplastic, an antimitotic, an antiplatelet, an anticoagulant, an antifibrin, an antithrombin, an antibiotic, an anti-allergic, an antioxidant substance, or any combination thereof;
and
wherein the second drug reduces inflammation, reduces the amount, the activity, or both the amount and the activity of tumor necrosis factor alpha, improves the responsiveness of the artery to insulin, reduces platelet activation, reduces fluctuation in hemoglobin A1C, reduces tissue factor activity, reduces thrombin activity, or any combination thereof.

29. The method of claim 28, wherein the first drug is selected from the group consisting of rapamycin (sirolimus), Biolimus A9, ridaforolimus, AP23572, tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin 40-O-[2-(2-hydroxyl)ethoxy]ethyl-rapamycin, 40-O-tetrazolylrapamycin, 40-epi-(N1-tetrazolyl)-rapamycin, myolimus, actinomycins, taxol, paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), dexamethasone, γ-hiridun, clobetasol, pimecrolimus, imatinib mesylate, midostaurin, and combinations thereof.

* * * * *